United States Patent [19]
Loubiere et al.

[11] Patent Number: 5,879,915
[45] Date of Patent: Mar. 9, 1999

[54] METHOD FOR THE NATURAL PRODUCTION OF FORMIC ACID OR FORMATE

[75] Inventors: Pascal Loubiere, Toulouse; Nicolas Lindley, Parisot; Emmanuel Vidor, St. Sebastien sur Loire; Patrick Taillade, Mouvaux, all of France

[73] Assignee: Lesaffre Developpement, Marcq En Baroeul, France

[21] Appl. No.: 805,577

[22] Filed: Feb. 25, 1997

[30] Foreign Application Priority Data

Feb. 26, 1996 [FR] France ................................. 96 02365

[51] Int. Cl.$^6$ ................................ C12P 7/64; C12P 7/62; C12P 7/56
[52] U.S. Cl. ..................... 435/135; 435/134; 435/139; 435/252.1; 435/252.3; 562/509
[58] Field of Search ................................ 435/252.1, 134, 435/139, 135, 252.3; 562/609

[56] References Cited

FOREIGN PATENT DOCUMENTS 0 322 010  11/1988  European Pat. Off. .
WO 95/19425  1/1995  WIPO .

OTHER PUBLICATIONS

"ATCC Bacteria & Bacteriophages" Edited Pienta et al Nineteenth Ed 1996 p. 199 Lactococcus.

"Fenaroli's Handbook of Flavor Ingredients", vol. II, 3rd Edition edited by George A. Burdock, Ph.D., CRC Press, pp. 231 and 280.

"Bactéries Lactiques", Coordinators H. De Roissart and F.M. Luquet, Edition Lorica, Jan. 1994, vol. 1, ISBN: 2–9507447–0–1, pp. 184 to 187, 242 to 257, 276 to 281 and 407.

Primary Examiner—Herbert J. Lilling
Attorney, Agent, or Firm—Henderson & Sturm

[57] ABSTRACT

The subject of the invention is the use, for the production of formic acid and/or formate starting from a culture medium containing a fermentable sugar, of a bacterial strain

- having a deficiency in the transportation or the metabolism of at least one fermentable sugar,
- containing an active degradation pathway for the preceding sugar via pyruvate formate lyase,
- capable of converting the preceding sugar mainly into formic acid and/or formate, even in the presence of a non-limiting concentration of said sugar.

It also relates to a fermentation process by culture of said strain with a view to the conversion of a fermentable sugar into formic acid or formate, as well as the culture media enriched with formic acid or formate thus obtained, as well as an extraction/purification process of the formic acid in the form of one of its volatile esters, preferably ethyl formate.

31 Claims, No Drawings

METHOD FOR THE NATURAL PRODUCTION OF FORMIC ACID OR FORMATE

Formic acid or methanoic acid is the first of the acids of the aliphatic series of carboxylic acids; it is a clear, colourless, strong-smelling and very aggressive liquid.

It has many uses in the leather or textile industries, and also as a preserving agent in silage making in which it acts by inhibiting the growth of moulds.

It is also used as an aromatic molecule in a large number of foods and drinks. Its esters, particularly ethyl formate, are also of great interest as aromatic molecules (FENAROLI's Handbook of Flavor Ingredients, Vol. 11, 3rd Edition CRC Press, p.280 and 231).

It is almost exclusively produced by chemical synthesis. It exists in the natural state; this molecule was discovered in 1670 amongst the products resulting from the distillation of ants. Formic acid is also found in a wide variety of plants, and it is produced as a natural aromatic substance for the flavouring industry by extraction from plants, in particular from nettles.

According to the United States of America regulations, or according to the European regulations (Council Directive No. 88-388/EEC on flavours), aromatic molecules obtained by micro-biological processes from a raw material of vegetable or animal origin also have the status of natural aromatic molecules. It appears that at present there is no commercially available formic acid corresponding to the standards of purity of aromatic molecules and prepared by a microbiological process, which can be explained by the fact that formic acid is well known to have antiseptic properties and therefore fermentation inhibiting properties at low doses (1 g/liter for *Escherichia coli*).

The work "Bactéries Lactiques", coordinators Roissart and Lucquet, Edition Lorica, January 1994, Vol. 1, ISBN reference: 2-9507447-0-1, provides a detailed description of the metabolic routes which lead lactic bacteria to produce either only lactic acid (homofermentary lactic bacteria) or lactic acid, acetic acid and ethanol (heterofermentary lactic bacteria), and sometimes other products such as formic acid, the latter however being formed in smaller quantities under very precise and limiting substrate conditions. This work may be considered as a virtually-exhaustive reference manual. The scientific terminology used hereafter is that of this work, and this work should be referred to for the explanation of all of the mechanisms and metabolic routes of lactic bacteria, in particular on pages 184 to 187, 242 to 257, 276 to 281, 407. The term "lactic bacteria" encompasses, as described in this work, bacteria belonging in particular to the Streptococcus, Lactococcus, Pediococcus, Lactobacillus and Bifidobacterium genera, it being understood that, contrary to "Bergey's Manual of Systematic Bacteriology" (1986), the Lactic Acid Streptococci, namely *Streptococcus lactis* and *Streptococcus raffinolactis* are called Lactococcus.

Document WO 95/19425 describes the use of bacterial strains of the Bacillus genus for the production by metabolic route of metabolites such as L(+)-lactate, as well as products other than L(+)-lactate, in particular ethanol, formate and acetate.

In the different examples and in the presence of an excess of glucose, mainly lactic acid is produced; on the contrary, in a medium with a limited amount of glucose and with a large excess of expensive growth factors (addition of twice as much of a "yeast extract/trypsic casein" mixture as of glucose), a fermentation medium is obtained having a final concentration of 2.5 g/liter of lactic acid, 5.5 g/liter of acetic acid, 4.1 g/liter of ethanol and 8.4 g/liter of formic acid.

Applicants have set themselves the aim of producing natural formic acid economically by microbiological route in such concentrations in the culture medium that it becomes easy to extract and purify in a form corresponding to the standards of the "Food Chemicals Codex" (National Academy Press, USA) and of the flavouring industry. Applicants noticed that this aim could be achieved using bacterial strains which they had the merit of selecting and which are capable of converting a non-limiting fermentable substrate into mainly formic acid or formate; they have also perfected a process using the bacterial strains in question.

The bacterial strains used according to the invention for the production of formic acid are characterized in that they:
are deficient in the transportation or the metabolism of at least one fermentable sugar,
contain an active degradation route for said sugar via pyruvate formate lyase,
are capable of converting said sugar mainly into formic acid, even in the presence of a non-limiting concentration of said sugar.

The bacterial strains in question have the surprising property of allowing a final concentration of formic acid or formate of higher than 10 g/liter to be obtained in the culture medium.

These bacterial strains are for example strains of homofermentary lactic bacteria deficient in their main membrane transportation system of lactose ("Phosphotransferase System Lactose" or also Lac PT//P-β-gal system) and the fermentation of which is not inhibited by formic acid up to at least 10 g/liter of formic acid.

These bacterial strains are preferably homofermentary lactic bacteria of the type of those in which the lactose transport is essentially determined by the genes carried by one or more lactose plasmids, said strains having the specific characteristic of not containing the plasmid or plasmids in question, without being lac⁻, i.e. without it being impossible for them to use lactose.

They belong in particular to the genus Lactococcus, more specifically to the species *Lactococcus lactis*.

One representative of this genus, belonging to the species *Lactococcus lactis*, variety lactis, is the strain deposited at the N.C.D.O. (National Collection of Dairy Organisms) now the N.C.F.B. (National Collection of Food Bacteria), previously in Reading, England, now in Aberdeen, Scotland, at following address: 23 St Machar Drive, Aberdeen AB2 1RY, Scotland, UK, under the No. 2118. This strain is denoted hereafter strain N.C.D.O. No. 2118.

From a general point of view, the bacterial strains used according to the invention are deficient, in at least one of their lactose transport systems, and very generally in their PTS ("Phospho-transferase system") lactose which is the main system in lactic bacteria, while having conserved the possibility of using lactose, they contain an active degradation route for pyruvate formed from lactose by pyruvate formate lyase and contain a DNA sequence capable of at least a 70%, and preferably of at least a 80% hybridization with the DNA of the N.C.D.O. strain N° 2118. These strains allow a final concentration, after anaerobic culture on lactose, of at least 10 g/liter of formic acid.

From an even more general point of view, the bacterial strains used according to the invention are strains which, on the one hand, under non-limiting conditions of a carbon-containing substrate, generally a fermentable sugar, use this carbon-containing substrate under anaerobiosis either without producing or only producing low intracellular quantities of fructose diphosphate, such that the conversion of the pyruvate formed from this carbon source into lactate is inhibited, or not very active at all, and that on the contrary most of the pyruvate formed is degraded by pyruvate formate lyase into formate, into ethanol and/or into acetate and which, on the other hand, allow production of at least 10 g/liter of formic acid in the culture medium, before being inhibited by the formic acid formed.

The fermentation process according to the invention for the preparation of formic acid or formate is characterized in that at least one of the strains used according to the invention is cultured under anaerobiosis on a culture medium containing, on the one hand, a carbon source consisting of a fermentable sugar in which said strain has a deficiency in transportation or in metabolism and, on the other hand, a nitrogen source, preferably a yeast extract.

According to an advantageous embodiment of the above process, the concentration in the culture medium of fermentable substrate is from 2 to 80 g/l, preferably from 5 to 60 g/l and more preferably from 10 to 30 g/l; its concentration of yeast extract is from 2 to 20 g/l, preferably from 5 to 20 g/l and more preferably from 8 to 12 g/l.

According to another advantageous embodiment of the above process, the nitrogen source is consisting of a mixture of amino acids essential to the growth of the bacterial strain used, with provision of the necessary vitamin complements.

According to another advantageous embodiment of the above process, the nitrogen source is constituted either by yeast extracts, or by meat extracts or by any peptone or any protein hydrolysate giving results equivalent to those obtained with the yeast extracts with regard to production of formic acid.

According to another advantageous embodiment of the above process, the temperature of the culture medium is 20° to 40° C., preferably 25° to 37° C. and more preferably 28° to 35° C., and its pH is 4 to 10, preferably 6.5 to 7.8 and more preferably 7 to 7.7.

According to a preferred embodiment of the above process, the fermentation is carried out by a discontinuous process with continuous supply of nutrients or "fed-batch", that is to say with progressive supply of the carbon source and complementary progressive supply of the nitrogen source, preferably consisting of yeast extracts. These progressive supplies will be carried out in such a way as to have in the culture medium for at least 90% of the fermentation time, a minimum of on the one hand at least 2 g/l of lactose and, preferably at least 5 g/l of lactose and, on the other hand, at least 2 g/l of yeast extract and, preferably, at least 5 g/l of yeast extract.

The invention also relates to, as new industrial products from which it is possible to isolate formic acid or formate, the culture media which can be obtained by implementing the process according to the invention and which are characterized by a formic acid or formate content of higher than 10 g/l, preferably higher than 20 g/l.

These culture media are also characterized in that the weight by weight (or in g/liter) ratio of formic acid or formate to lactic acid is higher than 1.

The content in these culture media of lactic acid or lactate is preferably lower than 10 g/l.

The invention will be able to be even better understood from the additional description which follows and from the non-limitative examples which relate to advantageous embodiments of certain aspects of the invention.

The inventors have shown that the bacterial strain of the type *Lactococcus lactis subsp.* lactis deposited at the N.C.D.O. under the N° 2118 is the typical strain to be used according to the invention.

They have also shown that this strain and the equivalent strains which are subjects of the invention, which are deficient in PTS ("Phosphotransferase system") lactose and capable of growing in particular on lactose as a fermentable carbon-containing substrate, produce preferentially formate, acetate and ethanol when they are cultured under anaerobiosis in the presence of lactose in a non-limiting quantity, that is to say from 10 to 80 g/l.

The formate yield relative to the lactose is surprisingly high; the formate concentration can reach up to 30 g/l before there is a total inhibition of the bacterial cells.

The presence in the culture medium of an excess of a nitrogen source constituted by hydrolysed proteins as well as vitamins and growth factors is required.

The nature of the nitrogen source is important in order to optimize the production of formic acid. The best results are obtained with yeast extracts which also have the advantage of promoting the growth of the bacteria and of delaying the inhibition of their metabolism by the formate formed, up to formate concentrations of at least 30 g/liter.

Other sources of nitrogen and vitamins may lead to almost equivalent results. In a general way, the man skilled in the art selects the peptone or the hydrolysate of proteins and the vitamin complements required as a function of their effectiveness and of their cost. Mixtures of amino acids and vitamins or growth factors can be envisaged, but they are much too expensive. Yeast extract is, amongst the sources of nitrogen and growth factors, the one which offers the best effectiveness/price ratio.

A yeast extract content of 10 g/l (for tested values from 2 to 30 g/l) seems to be the optimum value both for the growth and for the production of formate. This limited content allows competitively priced productions of formic acid.

The value of the concentration in the culture medium of fermentable substrate, in particular lactose, is important.

In fact, the formate yield is reduced from 2.26 to 1.42 moles per mole of lactose as the initial lactose concentration is increased from 5 to 70 g/l in a medium containing 10 g/l of yeast extract.

At the same time, the lactate yield increases to 0.64 mole per mole of lactose as the initial lactose concentration is increased from 5 to 70 g/l in a medium containing 10 g/l of yeast extract.

Surprisingly, it has been shown that the production of formic acid and of formate is all the better when, on the one hand, a medium is used which is rich in nitrogenous substances and in growth factors, which is in particular the case with a medium containing 10 g/liter of yeast extract and when, on the other hand, there is enough lactose to allow growth of the bacterial strain used, that is to say under conditions such that under no circumstances is a medium used which is limiting both with regard to the sources of nitrogen and of growth factors, and with regard to the carbon source, in this case lactose.

The pH value of the culture medium is also important.

Thus, when the pH rises from 5.86 to 7.25, an improvement in the formate yield is noted which goes from 2.09 to 2.39 moles per mole of lactose and, on the contrary, a negative effect is noted on the lactate yield which goes from 0.54 to 0.17 moles per mole of lactose.

The presence of mineral salts, in particular alkaline-earth salts such as $MgCl_2$, for example at a concentration of the order of 0.2 g/l, is advantageous. In a general way, it must be made sure that the medium is not lacking in mineral elements, including mineral oligo-elements.

The optimum temperature for encouraging the growth and yield of formate is 20° to 40° C. and, preferably, 28° to 37° C.

"Fed-batch" fermentation by the progressive addition of fermentable substrate, for example lactose, and of nitrogen source, for example yeast extract, such that a concentration of about 10 g/l of fermentable substrate, in particular lactose, and of about 10 g/l of nitrogen source, in particular yeast extract, is maintained for at least 80% of the fermentation time, allows the formate-producing phase to be prolonged and formate concentrations of 15 to 20 g/l to be obtained.

The progressive addition of nitrogen source and of fermentable substrate, in particular yeast extract and lactose, simultaneously with an increase of the pH from 7 to 7.7 by the addition of KOH, allows for example an even better increase of the final formate content to 30 g/liter and an increase in productivity to at least 0.5 g/l/hr.

To obtain a productivity of at least 0.5 g/l/hr and a concentration of formic acid higher than 20 g/l, preferably higher than 25 g/l, an essential condition is to seed the fermenter for the "fed-batch" production of formic acid with a sufficient amount of a biomass which is in an exponential phase growth.

"Fed-batch" fermentation is the preferred method for producing formic acid because it allows the optimum conditions for formic acid production to be constantly maintained in the culture medium, which conditions are linked with the growth of the biomass. It allows an optimum concentration of yeast extract and lactose to be maintained, adjustment of the pH to be obtained with the development of the pH as a function of the formic acid formed, the regulation of the pH having the effect in particular of reducing the inhibiting effect of the formic acid.

At the same time, the lactic acid and acetic acid concentrations are limited and are preferably at most 10 g/l and 15 g/l respectively, it being understood that the ratio of formic acid or formate to lactic acid or lactate produced is always higher than 1.

The preferential production of formate was also obtained in the presence of other fermentable substrates of the group comprising galactose, maltose, xylose, ribose and gluconic acid, the transportation and metabolism of which sugars or carbon-containing substrate do not lead, under anaerobiosis, with strains of the same type as the N.C.D.O. strain N° 2118 and, more generally, with lactic bacterial strains, to sufficient intracellular concentrations of FDP (Fructose Diphosphate) to significantly activate LDH (Lactate Dehydrogenase) leading to the conversion of the pyruvate formed into lactate, hence on the contrary an activation of the pyruvate formate lyase and a production of formate.

It was also noted that using the N.C.D.O. strain N° 2118, high concentrations of other fermentable substrates, in particular of saccharose, glucose, mannose, fructose and trehalose, lead under anaerobiosis to low formic acid contents, whilst lactic acid becomes predominant. In fact, the N.C.D.O. strain N° 2118 is not deficient in the transportation or the metabolism of these different sugars and consequently their entry leads to significant intracellular concentrations of FDP activating LDH which converts the pyruvate formed from these sugars into lactate.

To recover the formic acid from the culture medium, means may be used which are known to the man skilled in the art for the extraction of these products or equivalent products from organic media and/or for purification of the formic acid obtained by chemical synthesis, such as for example vacuum distillation.

This extraction or purification of formic acid or of formate salts starting from culture medium at the end of the fermentation stage is a very costly and delicate operation. Formic acid is a hydrophilic molecule, making difficult the extraction by solvents authorized for the extraction of flavourings. The separation of, on the one hand, acetic acid and, on the other hand, formic acid, which are initially in a mixture in aqueous solution, necessitates a very large number of theoretical distillation stages.

Another aspect of the invention is a complete process for the production of formic acid wherein it is extracted and purified in the form of a volatile ester such as ethyl formate. This complete process comprises the following steps:

elimination of bacteria and suspended particles in the culture medium, concentration by evaporation of the culture medium containing formic acid with steam distillation of a part of the acetic acid which is present, addition of an excess of alcohol, preferably of natural origin, this alcohol being preferably ethanol, distillation of the volatile ester thus formed, and recovery of pure formate, being preferably ethyl formate.

Preferably, the starting culture medium is left to acidify naturally at a pH between 4 and 5 at the end of fermentation. The elimination of bacteria and suspended particles is achieved by centrifugation, possibly with the help of a coagulating or a flocculating agent. The recovery yield of formic acid is at least 90% and, preferably, at least 97%.

The culture medium, once free of insoluble particles, is concentrated by a rapid evaporation method such as vacuum evaporation. Due to the difference in dissociation constants between formic, acetic and lactic acids, at least 70% of the acetic acid present, and preferably at least 80%, is carried away into condensates. On the contrary, at least 90% of the formic acid, and preferably at least 95%, is conserved in the concentrate. The concentrate obtained will preferably contain at least 100 g/l of formic acid, less than 20 g/l of acetic acid and about 40 to 50 g/l of lactic acid.

To this concentrate is added pure natural ethanol derived from the fermentation of the juice of sugar beet, in excess with respect to the amount necessary for the esterification of formic acid, for example three times the amount of that of formic acid.

The mixture is then introduced in the boiling portion of a distillation column and boiled. The ethyl formate is found at the top of the column from where it may be removed. This removal of ethyl formate displaces the esterification reaction in the direction of ethyl formate; after recycling, at least 80% and preferably at least 90% of the formic acid of the distilled mixture is recovered in the form of ethyl formate, having the required standard of purity of this aromatic molecule.

At least 65% and preferably at least 70% of the formic acid present in the starting culture medium is recovered in the form of ethyl formate.

In Examples 1 to 4 which follow, there are successively examined the influence on the culture of the N.C.D.O. strain N° 2118 (N.C.F.B. 2118)

of the composition of the culture medium, of the lactose concentration, of the pH, of the temperature.

In Example 5, a "fed-batch" production of formic acid according to the preferred embodiment of the invention has been described. In Example 6, a test for optimizing the "fed-batch" production of formic acid is described in order to improve the productivity of this production, the productivity being an essential economic criteria for the industrialization of biological processes. In Example 7, a preferred embodiment of the invention is described, leading to the production of natural ethyl formate having the purity standard required for aromatic molecules.

EXAMPLE 1

Influence of the Composition of the Culture Medium

First of all a general description of the materials and methods used is given, then the experiments carried out in culture reactors and tubes in order to study the influence of the composition of the culture medium, in particular the influence of the nitrogen and growth factor sources, are described.

I. Materials and methods

11) Strain used

The strain used is the strain *Lactococcus lactis subsp. lactis* N.C.D.O. N° 2118. This strain N.C.D.O. N° 2118 or N.C.F.B. 2118 was redeposited according to the Budapest Treaty at the "Collection Nationale de Cultures de Micro-organismes", Institut Pasteur, 25 rue du Docteur Roux, 75724 PARIS CEDEX 15, on Feb. 18, 1997 under the N° I-1849.

12) Media used

Three synthetic culture media were retained, called MCD, MS10 and MS14 respectively.

The composition of these three media is indicated in Table I.

TABLE I

Composition of the three synthetic media

|  | MCD (g/l) | MS10 (g/l) | MS14 (g/l) |
|---|---|---|---|
| Lactose | 10 | 10 | 10 |
| Na Acetate | 1 | — | — |
| NH$_4$ citrate | 0.6 | — | — |
| NH$_4$ sulphate | — | 0.6 | — |
| KH$_2$PO$_4$ | 9.0 (3.0) | 9.0 (3.0) | 9.0 (3.0) |
| K$_2$HPO$_4$ | 7.5 (2.5) | 7.5 (2.5) | 7.5 (2.5) |
| Amino acids |  |  |  |
| Alanine | 0.24 | 0.24 | — |
| Tryptophan | 0.05 | 0.05 | — |
| Tyrosine | 0.29 | 0.29 | — |
| Phenylalanine | 0.28 | 0.28 | — |
| Serine | 0.34 | 0.34 | 1.02 |
| Glycine | 0.17 | 0.17 | — |
| Cysteine | 0.17 | 0.17 | — |
| Histidine | 0.11 | 0.11 | — |
| Glutamine | 0.51 | 0.51 | — |
| Proline | 0.68 | 0.68 | — |
| Arginine | 0.12 | 0.12 | — |
| Threonine | 0.23 | 0.23 | — |
| Lysine | 0.35 | 0.35 | — |
| Asparagine | 0.34 | 0.34 | — |
| Methionine | 0.12 | 0.12 | 0.24 |
| Valine | 0.33 | 0.33 | 0.165 |
| Isoleucine | 0.20 | 0.20 | 0.20 |
| Leucine | 0.47 | 0.47 | 0.47 |
| Aspartate | — | — | — |
| Glutamate | — | — | 0.30 |
| Mineral salts |  |  |  |
| MgCl$_2$ · 6H$_2$O | 200 | 200 | 200 |
| FeCl$_2$ · 4H$_2$O | 5 | — | — |
| CaCl$_2$ · 2H$_2$O | 50 | — | — |
| ZnSO$_4$ · 7H$_2$O | 5 | — | — |
| CoCl$_2$ · 6H$_2$O | 2.5 | — | — |
| Bases |  |  |  |
| Adenine | 10 | — | — |
| Guanine | 10 | — | — |
| Uracil | 10 | — | — |
| Xanthine | 10 | — | — |
| Vitamins |  |  |  |
| p.a. benzoic acid | 10 | — | — |
| Biotin | 10 | 10 | 10 |
| Folic acid | 1 | — | — |
| Nicotinic acid | 1 | 1 | 1 |
| Panthotenic acid | 1 | 1 | 1 |
| Riboflavine | 1 | — | 1 |
| Thiamine | 1 | — | — |
| Pyridoxine | 2 | — | — |

TABLE I-continued

Composition of the three synthetic media

|  | MCD (g/l) | MS10 (g/l) | MS14 (g/l) |
|---|---|---|---|
| Cyanocobalamine | 1 | — | — |
| Orotic acid | 5 | — | — |
| 2-deoxythymidine | 5 | — | — |
| Inosine | 5 | — | — |
| D,L-6,8-thioctic acid | 2.5 | — | — |
| Pyridoxamine | 5 | 5 | 5 |

The concentrations used in the reactors or fermenters are indicated in brackets in Table I.

Also, a medium is used containing a high quality *Saccharomyces cerevisiae* yeast extract without salt, such as for example the yeast extract BIO SPRINGER®, a pure autolysate of *Saccharomyces cerevisiae* yeast, in powder form without salt, type "B", marketed by the Bio Springer Company, B.P. 17, 94701 Maisons-Alfort, France.

This medium has the following composition:

| Yeast extract | 10 g/l |
|---|---|
| Lactose | 50 g/l |
| MgCl$_2$ · 6H$_2$O | 0.2 g/l |
| KH$_2$PO$_4$ | 3.0 g/l |
| K$_2$HPO$_4$ | 2.5 g/l. |

The yeast extract provides all the amino acids, vitamins and growth factors.

13) Culture techniques

131) Preservation of the strain

From a sample of the N.C.D.O. strain N° 2118, a working batch is made on an MCD medium in culture tubes, as described hereafter.

The strain cultures are incubated at 30° C. until they reach an OD (optical density) close to 1.2 at 580 nm. This corresponds to the end of the exponential growth phase. These cultures are then mixed with 20% glycerol (at 80%), then stored at −20° C. after distribution into cryo-tubes of the NUNC® brand.

132) Preparation of the tubes

It is indicated that, according to the general technique for preparing the preculture or culture tubes, glass tubes for anaerobic cultures with a capacity of 20 ml are used. Beforehand, these tubes are degassed for 10 minutes with nitrogen, stopped with gas-impermeable stoppers, sealed, then sterilized at 121° for 20 minutes.

10 ml of each of the media identified in Table I (at pH=6.6) are introduced into the same number of tubes using syringes fitted with filters with a porosity of 0.2 μm, for example those of the MINISART® brand.

133) Precultures

Before each tube fermentation, a preculture is made on the same medium; to do this, the medium is inoculated at 4% by volume from a NUNC® brand cryo-tube and incubated at 30° C. on a platform shaker until an optimum OD is obtained (0.6 on MS14, 1.2 on MS10 and MCD at 580 nm). Using this preculture, a second preculture is inoculated at 4% by volume, the latter being carried out in the same way and used to inoculate the fermentation medium of the tube cultures described below with a culture in full growth phase, without providing elements other than those already contained in the medium.

134) Tube culture

The tubes containing the fermentation medium are thus inoculated with 0.4 ml of preculture made with the same medium; they are then placed on a platform shaker (120 rev/min) at 30° C. The growth kinetics is monitored every hour by measuring the OD at 580 nm using a tube spectrophotometer, for example that marketed by the PROLABO Company under the reference 320-RD.

135) Discontinuous cultures in stirred reactors

The fermenters used are those marketed under the brand SETRIC 2N, SET series with an autoclavable glass collar; their useful capacity is from 0.5 to 2 liters. The stirring, the temperature and the pH are adjusted by control modules, for example those marketed under the SETRIC brand.

During the fermentations, the conditions are as follows:

stirring: 250 rev/min, temperature: 30° C., maintained by a proportional-action control valve which controls a heating baffle or an electrovalve connected to a cooling circuit, pH: adjusted to 6.6 by a proportional control; the probe used, for example that of the INGOLD brand, is calibrated prior to sterilization, which takes place mounted on the fermenter. The solution for adjusting the pH is constituted by 10N KOH.

Before use, the fermenter is sterilized with about 1 liter of distilled water at 121° C. for 20 minutes.

Then the fermenter is equipped and then sterilized again.

The water is then evacuated and a quantity of 1.6 l of the medium defined above is introduced by means of a glass connector attached to a silicon tube.

Sterilization of the medium is carried out at the same time by filtration on a filtration cartridge, for example that of the SARTORIUS brand, attached to the connector.

Next, the culture medium is degassed for 30 minutes by bubbling through nitrogen, stirring being carried out.

Throughout the fermentation, a nitrogen pressure of 20 mbars is maintained by a manometric pressure-reducing valve connected to the nitrogen bottle.

Precultures (300 ml) are made in 500 ml bottles but, in contrast to the procedure followed for the tube fermentations, the cells are concentrated during the second preculture by centrifuging to about one sixth of the initial volume of the supernatant.

The fermenter is then inoculated with the washed and concentrated preculture using a 50 ml sterile syringe.

This operation allows an OD of about 0.2 units to be obtained at the time of the inoculation.

II. Studies of the influence of the culture medium

21) Experiments in stirred discontinuous reactors

In a first experiment in a SETRIC fermenter, a stirred discontinuous culture is carried out over 10 hours with the MS10 medium. 4 g/liter of formate is obtained, that is a formate yield of 3.24 moles per mole of lactose, very close to the theoretical yield of 4 moles of formic acid per mole of lactose by the pyruvate formate lyase pathway. The lactate production is negligible.

In a second experiment, the SETRIC fermenters are used with the following culture media:

the synthetic media MS14, with 50 g/liter of lactose instead of 10 g/liter, which is a minimal medium;

the synthetic medium MS10, with 50 g/liter of lactose instead of 10 g/liter, called limited AA medium MS10*;

the synthetic medium MS10, with 50 g/liter of lactose and at the same time multiplication of the amino acid concentration by 5, called excess AA MS10**;

the medium with yeast extract as described above.

The results of these four fermentations are given in Table II.

TABLE II

|  | MS14 | Limited AA MS10* | Excess AA MS10** | Yeast extract |
|---|---|---|---|---|
| Formate mM (g/l) | 115 | 96 | 133 | 255 |
|  | (5.2) | (4.3) | (6.0) | (11.5) |
| Lactate mM (g/l) | 138.5 | 175 | 157 | 79.5 |
|  | (12.3) | (15.6) | (14.0) | (7.1) |
| Formate yield (mol/mol) | 0.91 | 0.74 | 1.06 | 2.04 |
| Lactate yield (mol/mol) | 1.10 | 1.36 | 1.25 | 0.63 |
| Duration (hr) | 65 | 82 | 100 | 48 |
| Formate productivity mM/h (g/l/hr) | 1.77 (0.08) | 1.17 (0.052) | 1.34 (0.06) | 5.3 (0.24) |
| Lactose consumed (g/l) | 43 | 44.1 | 43 | 42.8 |
| Yeast extract (g/l) at the start | 0 | 0 | 0 | 10 |
| Lactose (g/l) at the start | 50 | 50 | 50 | 50 |

Three phases can be distinguished during these four fermentations with 50 g/liter of lactose, the overall results of which are given in Table II.

A first phase which lasts for about ten hours, during which, except on the minimal medium MS14, there is practically solely production of formate; the reason for this is that it is only or almost only the pyruvate formate lyase pathway which is made use of. With medium MS14, there is a lactate production from the start of the culture. In this first phase, the concentration and the productivity of formate increase with the richness of the medium in nutritive elements. This observation shows a link between, on the one hand, the metabolism of the lactic bacteria and, on the other hand, the concentration and/or the composition of the amino acids.

A second phase during which there is production of formate and lactate; this second phase stops with the end of the biomass growth.

A third phase during which, except with the medium containing yeast extract, the formate production is stopped, only lactate being produced until the lactose is used up. This is a static phase for the biomass of bacteria. On a synthetic medium, the formate production must be stopped in order to obtain improved productivities at the end of the second phase, that is after 50 hours on the MS14 medium, 35 to 40 hours on the two MS10 media.

An improved productivity is noted of the formate production on the medium containing yeast extract, on the one hand, during each of the phases and, on the other hand, overall during the entire fermentation period.

22) Tube cultures for studying different nitrogen sources

The maximum growth rate $\mu$max(hr$^{-1}$) as a function of the nature of the nitrogen source is determined by tube culture.

To do this, media were used which all contain 10 g/l of lactose and 0.2 g/l of $MgCl_2 \cdot 6H_2O$ and having a pH of 6.6 (supplied by the phosphate buffer for tube cultures), the nitrogen source (present in a quantity of 10 g/l) being successively consisting of yeast extract (ye)

gelatin trypsic peptone (gtp)

tryptone (t)

meat extract (me)

soya peptone (sp)

atomized corn-steep (acs)

casein trysic peptone (ctp) and malt extract (mae).

In each case, the $\mu$max(hr$^{-1}$) and the yield Y of formate and of lactate, expressed in mol/mol, are determined.

The results recorded are set out in Table III.

TABLE III

| | Nutritive element (at 10 g/l) | | | | | | | |
|---|---|---|---|---|---|---|---|---|
| | ye | gtp | t | me | sp | acs | ctp | mae |
| $\mu$max(hr$^{-1}$) | 0.64 | 0.53 | 0.30 | 0.37 | 0.74 | 0.16 | 0.31 | 0.50 |
| Y formate mol/mol | 2.58 | 2.35 | 2.29 | 2.16 | 1.75 | 1.63 | 1.26 | no formate |
| Y lactate mol/mol | 1.02 | 1.82 | 1.79 | 0.62 | 1.12 | 1.15 | 2.70 | |

Examination of the results set out in Table III shows the observation that yeast extract promotes growth and allows the best formate yield; it confirms the importance of the nitrogen source and of the growth factors. These results show that the man skilled in the art must carefully select his nitrogen source and growth factors.

With the same medium at 10 g/liter of lactose, the concentration of yeast extract in the tube cultures was varied from 2 to 30 g/liter; this concentration is at its optimum, for both the growth rate and also the yield in moles of formate/mole of lactose, between 5 to 20 g/liter and more particularly at about 10 g/liter, at which concentration the best growth rate and the best yield are obtained.

EXAMPLE 2

Influence of the Lactose Concentration

The culture medium used is that containing 10 g/liter of yeast extract and described in Example 1, apart from the difference that the lactose concentration is fixed successively at 5, 10, 20, 30, 50, 70 and 100 g/l.

The culture technique used is the tube culture technique described in example 1.

For each of the lactose concentrations:
the maximum growth rate or $\mu$max per hour,
the formate yield expressed in moles of formate per mole of lactose,
the lactate yield expressed in moles of lactate per mole of lactose
are determined.

The results obtained are set out in Table IV.

TABLE IV

| | Lactose concentration in g/l | | | | | | |
|---|---|---|---|---|---|---|---|
| | 5 | 10 | 20 | 30 | 50 | 70 | 100 |
| Maximal growth rate in hr-1 | 0.87 | 0.86 | 0.97 | 0.87 | 0.88 | 0.87 | 1.0 |
| Formate yield mol/mol | 2.26 | 2.43 | 1.64 | 1.91 | 1.67 | 1.42 | — |
| Lactate yield mol/mol | 0.31 | 0.33 | 0.42 | 0.58 | 0.74 | 0.63 | — |

Examination of the values found and set out in Table IV shows that the growth rate varies little with the lactose concentration, that the formate concentration is predominant relative to the lactate concentration up to 70 g/l and that the formate yield is at maximum at 10 g/l of lactose.

EXAMPLE 3

Influence of the pH

The culture medium based on 10 g/liter of yeast extract described in the previous examples is used, the lactose content being 10 g/liter.

The culture technique is the tube culture technique described in Example 1.

For eight pH values, namely 5.86–6.15–6.5–6.86–7–7.25–7.57 and 8, the maximal growth rate per hour and the yield of formate and of lactate, expressed in moles per mole of lactose, are determined.

The values found are set out in Table V.

TABLE V

| | pH | | | | | | | |
|---|---|---|---|---|---|---|---|---|
| | 5.86 | 6.15 | 6.5 | 6.86 | 7 | 7.25 | 7.57 | 8 |
| Maximal growth rate in hr-1 | 0.76 | 0.75 | 0.86 | 0.86 | 0.89 | 0.82 | 0.78 | 0.6 |
| Formate yield mol/mol | 2.09 | 2.15 | 2.43 | 2.46 | 2.38 | 2.39 | — | — |
| Lactate yield mol/mol | 0.54 | 0.35 | 0.33 | 0.27 | 0.21 | 0.17 | — | — |

Examination of the values set out in Table V shows that the optimum pH for growth is 7, that the formate yield is improved at a pH>6.5 and that the lactate yield decreases with the increase in the pH.

EXAMPLE 4

Influence of the Temperature

The culture medium containing 10 g/liter of yeast extract, 10 g/liter of lactose, 0.2 g/liter of $MgCl_2$ and the phosphate buffer giving a pH of 6.6 for tube cultures, already used in the previous examples, and the tube culture technique described in Example 1 are used.

The maximal growth rate per hour and the yields (in mol/mol) of formate and of lactate are determined.

The results are set out in Table VI.

TABLE VI

| | Temperature in °C. | | | |
|---|---|---|---|---|
| | 21 | 30 | 37 | 45 |
| Maximal growth rate (hr-1) | 0.35 | 0.66 | 0.60 | 0.16 |
| Formate yield mol/mol | 2.31 | 2.26 | 2.41 | 1.34 |
| Lactate yield mol/mol | 0.46 | 0.41 | 0.47 | 1.30 |

Examination of the values set out in Table VI shows that the optimal temperature is 30° to 37° C. The temperature of 30° C. generally used in the different examples is optimal for growth whilst preserving a good formate yield.

EXAMPLE 5

"Fed-batch" Cultures in Stirred Fermenters

Relative to the "batch" cultures described in the previous examples where all of the culture medium is added before the start of fermentation, "fed-batch" culture consists of first adding the different elements of the culture medium at the start, then continuously or semi-continuously so as to maintain in the fermentation medium the concentrations judged to be optimal, both for the carbon source, here lactose, and also for the nitrogen source and growth factors, here yeast extract.

The "fed-batch" fermentations under anaerobiosis are carried out using fermenters of the SETRIC brand described in Example 1 according to the operating conditions described in Example 1, except for the following specific conditions corresponding to "fed-batch" cultures.

The initial culture medium is the following, before seeding with the biomass of the N.C.D.O. strain N° 2118:

| | |
|---|---|
| Initial yeast extract | 10 g/l |
| Initial lactose | 30 g/l |
| Initial pH | 7 |
| $MgCl_2 \cdot 6H_2O$ | 0.2 g/l |
| $KH_2PO_4$ | 1.67 g/l |
| $K_2HPO_4$ | 3.33 g/l |
| Temperature | 30° C. |

Within the scope of the principle of "fed-batch" culture, the additions of the yeast extract are made using a solution of yeast extract at 300 g/liter and those of lactose using a solution of lactose at 500 g/liter.

The pH is adjusted from 7 to 7.7, with a regular rise by steps of 0.2 unit through the addition of KOH.

The yeast extract is added continuously or semi-continuously after 10 hours of fermentation, so as to maintain a maximal growth of the bacterial biomass for as long as possible due to an equivalent minimal concentration of assimilatable amino acids and growth factors provided by the yeast extract of at least 2 g/liter and preferably of at least 5 g/liter of yeast extract in the culture medium.

This addition of yeast extract is stopped when the biomass moves into the static phase.

The supply in lactose starts as soon as the residual lactose is 5 g/liter and the lactose concentration is maintained at 5 g/liter until the end of the fermentation.

The duration of the experiment is 42 hours.

The results of the measurements carried out after 42 hours are set out in Table VII.

TABLE VII

| | |
|---|---|
| Formate (g/l) | 22 |
| Formate yield mol/mol of lactose | 2.93 |
| Lactate (g/l) | 8.1 |
| Lactate yield mol/mol of lactose | 0.55 |
| Acetate (g/l) | 13.5 |
| Acetate yield mol/mol of lactose | 1.37 |
| Ethanol (g/l) | 10.6 |
| Ethanol yield mol/mol of lactose | 1.40 |
| Biomass dry extract (g/l) | 5.52 |

Examination of the results set out in Table VII shows that "fed-batch" fermentation allows a very good formate yield, close to 3 moles of formate per mole of lactose, and a high concentration, higher than 20 g/liter of formate.

EXAMPLE 6

Optimization of the "Fed-Batch" Culture and Extrapolation of the Method to a More Important Scale The improvement in the productivity is an essential factor for the financial feasibility of a biochemical process. The parameters having an influence on the productivity are the supply profits of the substrates, the maintainance of optimal conditions of functioning of the biocatalyst, the quantity of biocatalyst, i.e. the quantity of biomass of the strain N.C.D.O. 2118.

The fermentations are achieved herein in "fed-batch" mode in anaerobiosis using fermenters of the SETRIC brand described in example 1, under functioning conditions identical to those described in example 5, reproduced in the test 1 which serves as a referrence, with the difference that the following specific conditions relative in particular to the quantity of biocatalyst and the composition of the preculture medium of the biocatalyst.

Test 2 was carried out by modifying only the preculture medium whereas test 3 was performed with the preculture medium modified and an increase in the seeding quantity.

The preculture medium for the production of biomass in tests 2 and 3 is that described in table VIII hereafter.

The preculture or production of the seeding biomass is carried out in batch mode or discontinuous mode under the same conditions as those described in example 1, the pH of the preculture medium being controlled at 7 in the 3 tests.

TABLE VIII

Preculture medium of tests 2 and 3

| Components | % |
|---|---|
| Peptone (Oxoid ®) | 1 |
| Lemco (Oxoid ®) | 0.8 |
| Yeast extract | 0.3 |
| $KH_2PO_4$ | 0.25 |
| $K_2HPO_4$ | 0.25 |
| $MgSO_4 7H_2O$ | 0.02 |
| $MnSO_4 4H_2O$ | 0.005 |
| Glucose | 0.5 |
| Lactose | 0.5 |

The peptone OXOID® and the meat extract LEMCO OXOID® are supplied by the Firm UNIPATH, F-69572 DARDILLY.

The culture is carried out in "fed-batch" mode under the same conditions as those of example 5, with the difference that the initial concentration in lactose is reduced to 25 g/l as opposed to 30 g/l. The seeding obtained from the preculture is in exponential growth phase and represents in volume a proportion of 4% (tests 1 and 2) or 16% (test 3) of the final volume of the culture medium.

The additions of concentrated solution of lactose and yeast extract are identical to those in example 5.

The hourly productivity is calculated by dividing the concentration of formate obtained by the duration of fermentation.

The results obtained are those in table IX hereafter:

TABLE IX

| | TEST 1 | | TEST 2 | | TEST 3 | |
|---|---|---|---|---|---|---|
| age t, hours | formate P, g/kg | productivity P/t, g/kg/hr | formate P, g/kg | productivity P/t, g/kg/hr | formate P, g/kg | productivity P/t, g/kg/hr |
| 15 | 3.1 | 0.21 | 5.6 | 0.37 | 12.2 | 0.81 |
| 20 | 7.4 | 0.37 | 12.1 | 0.61 | 16.1 | 0.81 |
| 25 | 11.6 | 0.46 | 15.2 | 0.61 | 19.8 | 0.79 |
| 30 | 14.1 | 0.47 | 17.6 | 0.59 | 21.6 | 0.72 |
| 35 | 17.2 | 0.49 | 19.5 | 0.56 | | |
| 37 | 19.2 | 0.48 | 21.5 | 0.54 | | |
| 42 | 21.6 | 0.48 | | | | |

It can be deduced from a comparison of tests 1 and 2 that there is an improvement of 20% of productivity of formic acid or formate due to a seeding biomass in exponential phase favoured by a richer preculture medium.

From a comparison of tests 1 and 3, a doubling of the average productivity is noted, from 0.4–0.5 g/kg/hr to 0.8–0.9 g/kg/hr of formate. In all the tests, the final concentration of formate is higher than 20 g/l. The duration of the fermentation is respectively 42 hours for test 1, 37 hours for test 2, and 30 hours for test 3.

The improvements in productivity so obtained allow a greater production with the same capacity of fermentation.

These tests were confirmed in fermenters of 8 liters useful capacity and then according to protocols where the seeding biomass was produced in a first fermenter of 8 liters by a batchwise process for seeding a second fermenter where the production of formic acid is achieved in "fed-batch".

The production of seeding biomass (i.e. biocatalyst) is carried out with a regulation of pH in such a manner that it is maintained at a pH 7 which corresponds to an optimum of growth for the bacteria, the pH being regulated either by NaOH or KOH. The transferts of culture should always be effected with biomasses in exponential growth phase and in strict anaerobiosis.

EXAMPLE 7

Extraction of Formic Acid by Esterification—Production of Ethyl Formate

In a 20 liters fermenter, the production of formic acid is carried out as described in example 6. The regulation of pH is stopped at the end of fermentation in a manner such that the culture medium acidifies naturally. A culture medium having the acid composition as follows is obtained:

| Formic acid | 20–22 g/l | |
|---|---|---|
| Acetic acid | 15 g/l | |
| Lactic acid | 7–14 g/l | (preferably less than 10 g/l) |
| pH | 4.5 | |

3 kg of fermentation material is used.

1) Centrifugation

This operation is carried out on a laboratory centrifuge of JOUAN® brand. To improve the separation of bacteria and possible other solid matters in suspension, a coagulent is preferably used, such as Laviron® N Special supplied by the Firm Les Produits Chimiques du Sidobre Sinnova, F-77981 Saint-Fargeau-Ponthierry, in the amount of 10 g/l of fermentation material.

The weight of supernatant is 2,900 g.

The recovery yield of formic acid in these operations is 97% in the supernatant.

2) Concentration of the wort

The quantity of supernatant used is 2,900 g.

The concentration of the supernatant is achieved by vacuum flash evaporation using laboratory equipment of the HEIDOLPH OB 2001® brand having an evaporating capacity of 0.5 l/hr evaporated water. The supernatant is heated to a maximum of 50° C. (P=50 mbar).

Due to the difference in dissociation constantes of formic and acetic acids, it is possible, in function of the pH, to preferentially remove acidic acid with respect to formic acid to the condensates. 70% of the acetic acid is found in the condensates, whereas more than 90% of the formic acid is found in the concentrated wort.

The concentrated supernatant obtained has the following average composition:

| Formic acid | 100 g/l |
|---|---|
| Acetic acid | 20–25 g/l |
| Lactic acid | 50–80 g/l. |

The recovery yield of formic acid for this stage is 90%. The supernatant obtained has a weight of about 500 g.

3) Esterification—distillation of ethyl formate

The weight of solution used in this step is 500 g.

This solution is mixed with ethanol. The amount of ethanol is three times higher than that of the formic acid present in the concentrated supernatant. Thus, 30 g of ethanol is added per 100 g of supernatant. The mixture is introduced into the boiler of a distillation column, and heated up to boiling.

The ethyl formate thus formed being very volatile (boiling temperature=54° C.), it is found at the head of the column. When the temperature of the head of the column stabilizes around 52°–53° C., the ethyl formate is removed. This removal is adjusted so as to maintain a constant temperature in the head of the column.

The fact of removing the ethyl formate as it is formed allows the displacement of the equilibrium of the esterification reaction, and to achieve a yield of 90%.

The ethyl formate obtained has the following average characteristics:

| Ethyl formate | 98% |
|---|---|
| Water content | 1–2% |
| Ethanol | traces |
| Ethyl acetate | traces. |

The distillation yield of the pure product is of the order of 70%.

The intermediate fraction, rich in ethyl formate and ethanol which remains at the bottom of the boiler, may be recycled during the subsequent esterifications. By way of the recycling, it is possible to recover as ethyl formate about 90% of the formic acid used.

These non-limitative examples show that the invention allows the production of formic acid and formate esters, especially ethyl formate, having the status of aromatic natural molecules according to the Code of Federal Regulations 21 Food and Drugs or Council Directive n° 88 388/EEC on flavours and to the norms of Food Chemicals Codex.

We claim:

1. A process for the production of formic acid and/or formate starting from a culture medium containing a carbon source consisting of at least one fermentable sugar, comprising fermentation of the said fermentable sugar by culture on the said culture medium of a bacterial strain which is deficient in the transportation or the metabolism of said fermentable sugar, which contains an active degradation pathway for the said sugar via pyruvate formate lyase, and which is capable of converting the said sugar mainly into formic acid and/or formate, even in the presence of a non-limiting concentration of said sugar.

2. Process according to claim 1, wherein the said bacterial strain permits obtaining in the culture medium of a final formic acid and/or formate concentration of higher than 10 g/l.

3. Process according to claim 1, wherein the said bacterial strain is a homofermentary lactic bacterium of the type of those in which the lactose transport is determined predominantly by the genes carried by one or more lactose plasmids, said strain having the specific characteristic of not containing the plasmid(s) in question, while still having the possibility of using lactose.

4. Process according to claim 1, wherein the bacterial strain belongs to the genus Lactococcus.

5. Process according to claim 1, wherein the bacterial strain belongs to the species *Lactococcus lactis*.

6. Process according to claim 1, wherein the bacterial strain belongs to the species *Lactococcus lactis*, variety lactis deposited at the N.C.D.O. (National Collection of Dairy Organisms) under the N° 2118.

7. Process according to claim 1, wherein the bacterial strain is deficient in at least one of its lactose transport systems, contains an active degradation pathway for pyruvate formed from the lactose by pyruvate formate lyase and contains a DNA sequence capable of at least a 70% hybridization with the DNA of the N.C.D.O. strain N° 2118.

8. Process according to claim 1, wherein the bacterial strain is deficient in its PTS ("Phosphotransferase system") lactose, contains an active degradation pathway for pyruvate formed from the lactose by pyruvate formate lyase and contains a DNA sequence capable of at least a 70% hybridization with the DNA of the N.C.D.O. strain N° 2118.

9. Process according to claim 1, wherein the bacterial strain is deficient in at least one of its lactose transport systems, contains an active degradation pathway for pyruvate formed from the lactose by pyruvate formate lyase and contains a DNA sequence capable of at least a 80% hybridization with the DNA of the N.C.D.O. strain N° 2118.

10. Process according to claim 1, wherein the culture of the bacterial strain is carried out under anaerobiosis and wherein the culture medium contains a nitrogen source.

11. A process according to claim 1, wherein said culture medium comprises a nitrogen source selected from the group consisting of a yeast extract, a meat extract, a peptone and a protein hydrolysate which gives, for the production of formic acid, results equivalent to that of the yeast extract.

12. Process according to claim 1, wherein the concentration in the culture medium of fermentable substrate is from 2 to 80 g/l, its yeast extract concentration being from 2 to 20 g/l.

13. Process according to claim 1, wherein the esconcentration in the culture medium of fermentable substrate is from 5 to 60 g/l, its yeast extract concentration being from 5 to 20 g/l.

14. Process according to claim 1, wherein the concentration in the culture medium of fermentable substrate is from 10 to 30 g/l, its yeast extract concentration being from 8 to 12 g/l.

15. Process according to claim 1, wherein the temperature of the culture medium is from 20° to 40° C. and wherein the pH is from 4 to 10.

16. Process according to claim 1, wherein the temperature of the culture medium is from 25° to 37° C. and wherein the pH is from 6.5 to 7.8.

17. Process according to claim 1, wherein the temperature of the culture medium is from 28° to 35° C. and wherein the pH is from 7 to 7.7.

18. Process according to claim 1, wherein the production of formic acid or formate is carried out in a "fed-batch" manner.

19. A process according to claim 1, wherein the production of formic acid or formate is carried out in a "fed-batch" manner comprising making progressive additions to the culture medium during the production of formic acid so s to have, for at least 90% of the fermentation time, in the culture medium a minimum of at least 2 g/l of lactose and of at least 2 g/l of yeast extract.

20. A process according to claim 1, wherein the production of formic acid or formate is carried out in a "fed-batch" manner comprising making progressive provisions of the culture medium during the production of formic acid so as to have, for at least 90% of the fermentation time, in the culture medium a minimum of at least 5 g/l of lactose and of at least 5 g/l of yeast extract.

21. A process according to claim 1, wherein the production of formic acid or formate is carried out in a "fed-batch" manner comprising making progressive supplies of the culture medium during the production formic acid are made so as to have, for at least 80% of the fermentation time, in the culture medium a minimum of at least 10 g/l of lactose and of at least 10 g/l of yeast extract.

22. The fermentate produced by the process according to claim 1 and having a formic acid or formate content of higher than 10 g/l.

23. The fermentate produced by the process according to claim 1 and having a formic acid or formate content of higher than 20 g/l.

24. The fermentate according to claim 23, wherein the ratio formic acid or formate to lactic acid or lactate is higher than 1.

25. The fermentate according to claim 23 having a lactic acid content lower than or equal to 10 g/l.

26. Process according to claim 1, comprising extracting or purifying the formic acid in the form of a volatile ester.

27. Process according to claim 1, comprising extracting or purifying the formic acid in the form of ethyl formate.

28. Process according to claim 1, comprising the steps of:

eliminating bacteria and suspended particles from the culture medium, concentrating by evaporation of the culture medium with steam distillation of a part of the acetic acid which is present, adding alcohol, distilling the volatile ester so formed, and recovering the formate in the form of a pure ester.

29. Process according to claim 1, comprising the steps of:

providing the culture medium containing formic acid with a pH from 4 to 5, eliminating bacteria and suspended particles from the culture medium, concentrating by evaporation of the culture medium with steam distillation of a part of the acetic acid which is present, adding natural ethanol in excess, distilling the volatile ester so formed, and recovering the formate in the form of a pure ester.

30. Process according to claim 1, comprising the steps of:

providing the culture medium containing formic acid with a pH from 4 to 5, separating the insoluble particles by centrifugation, concentrating by vacuum evaporation, adding ethanol in excess and distilling the ethyl formate, recycling the ethyl formate not recovered during a first distillation, so as to recover in the form of ethyl formate at least 65% of the formic acid present in the culture medium.

31. Process according to claim 1, comprising the steps of:

providing the culture medium containing formic acid with a pH from 4 to 5, separating the insoluble particles by centrifugation, concentrating by vacuum evaporation, adding ethanol in excess and distilling the ethyl formate, recycling-the ethyl formate not recovered during a first distillation, so as to recover in the form of ethyl formate at least 70% of the formic acid present in the culture medium.

* * * * *